(12) United States Patent
Fujitani (10) Patent No.: US 10,149,608 B2
(45) Date of Patent: Dec. 11, 2018

(54) BENDING PORTION FOR ENDOSCOPE AND ENDOSCOPE INCLUDING BENDING PORTION FOR ENDOSCOPE

(71) Applicant: OLYMPUS CORPORATION, Tokyo (JP)

(72) Inventor: Kiwamu Fujitani, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 63 days.

(21) Appl. No.: 15/355,138

(22) Filed: Nov. 18, 2016

(65) Prior Publication Data

US 2017/0065153 A1 Mar. 9, 2017

Related U.S. Application Data

(63) Continuation of application No. PCT/JP2015/071319, filed on Jul. 28, 2015.

(30) Foreign Application Priority Data

Sep. 22, 2014 (JP) ................................. 2014-192920

(51) Int. Cl.
*A61B 1/00* (2006.01)
*A61B 1/005* (2006.01)
(Continued)

(52) U.S. Cl.
CPC ............ *A61B 1/0057* (2013.01); *A61B 1/008* (2013.01); *A61B 1/0051* (2013.01);
(Continued)

(58) Field of Classification Search
CPC ................ A61B 1/0055; A61B 1/0057; A61B 2017/00309; A61B 1/005; A61B 1/0051;
(Continued)

(56) References Cited

U.S. PATENT DOCUMENTS 4,911,148 A * 3/1990 Sosnowski ........... A61B 1/0056
600/136
6,749,560 B1 * 6/2004 Konstorum .......... A61B 1/0055
600/139
(Continued)

FOREIGN PATENT DOCUMENTS

EP 1867270 A1 12/2007
EP 2446802 A1 5/2012
(Continued)

OTHER PUBLICATIONS

International Search Report dated Oct. 13, 2015 issued in PCT/JP2015/071319.

*Primary Examiner* — Timothy J Neal
*Assistant Examiner* — Aaron B Fairchild
(74) *Attorney, Agent, or Firm* — Scully, Scott, Murphy & Presser, P.C.

(57) ABSTRACT

A bending portion for endoscope includes: a distal end side bending tube in which a plurality of bending pieces are continuously and pivotably coupled; a proximal end side bending tube coupled to a proximal end side of the distal end side bending tube and including a bending element with a bending moment for obtaining a predetermined bending angle greater than a bending moment of the distal end side bending tube; and an operation wire actively bending the distal end side bending tube and the proximal end side bending tube by pulling and relaxing, wherein pulling and relaxing of the operation wire actively bend the distal end side bending tube and the proximal end side bending tube.

6 Claims, 8 Drawing Sheets

(51) Int. Cl.
  *A61B 1/008*  (2006.01)
  *A61M 25/01*  (2006.01)
  *A61M 25/00*  (2006.01)
  *A61B 1/267*  (2006.01)
  *G02B 23/24*  (2006.01)
  *A61B 17/00*  (2006.01)

(52) U.S. Cl.
  CPC ........ *A61B 1/0055* (2013.01); *A61B 1/00112* (2013.01); *A61B 1/2676* (2013.01); *A61M 25/0013* (2013.01); *A61M 25/0138* (2013.01); *G02B 23/2476* (2013.01); *A61B 2017/00309* (2013.01); *A61M 2025/0161* (2013.01)

(58) Field of Classification Search
  CPC ................ A61B 1/008; A61B 1/00071; A61M 25/0013; A61M 25/0053; A61M 25/0138; A61M 2025/0161
  See application file for complete search history.

(56) References Cited

U.S. PATENT DOCUMENTS

| | | | |
|---|---|---|---|
| 2006/0200000 A1* | 9/2006 | Sato | ............... A61B 1/0055 600/146 |
| 2008/0214897 A1 | 9/2008 | Matsuo | |
| 2010/0280449 A1* | 11/2010 | Alvarez | ........... A61B 17/00234 604/95.04 |
| 2011/0282153 A1 | 11/2011 | Ueki | |

FOREIGN PATENT DOCUMENTS

| | | |
|---|---|---|
| JP | 2006-218232 A | 8/2006 |
| JP | 2010-117727 A | 5/2010 |
| WO | WO 2006/085621 A1 | 8/2006 |
| WO | WO 2011/092937 A1 | 8/2011 |
| WO | WO 2012/035531 A1 | 3/2012 |
| WO | WO 2013/190910 A1 | 12/2013 |

* cited by examiner

BENDING PORTION FOR ENDOSCOPE AND ENDOSCOPE INCLUDING BENDING PORTION FOR ENDOSCOPE

CROSS REFERENCE TO RELATED APPLICATION

This application is a continuation application of PCT/JP2015/071319 filed on Jul. 28, 2015 and claims benefit of Japanese Application No. 2014-192920 filed in Japan on Sep. 22, 2014, the entire contents of which are incorporated herein by this reference.

BACKGROUND OF THE INVENTION

1. Field of the Invention

The present invention relates to a bending portion for endoscope configured to perform bending action according to operation of an operation member provided on an operation portion and to an endoscope including the bending portion for endoscope.

2. Description of the Related Art

In recent years, a medical device, such as an endoscope, inserted into a subject has been widely used in a medical field and an industrial field.

Particularly, in the endoscope used in the medical field, an elongated insertion portion is inserted into a body cavity that is a subject. An organ in the body cavity can be observed, and various treatments can be performed by using a treatment instrument inserted into an insertion channel of a treatment instrument included in the endoscope as necessary.

In a well-known configuration of the insertion portion of the endoscope, a bendable bending portion is provided to improve a property of insertion into the subject. A bending tube including a plurality of pivotably coupled bending pieces is included inside of a conventional bending portion, and the bending portion is bent by remotely operating turns of the plurality of bending pieces.

By the way, in an endoscope inserted into branched and complicated bronchi or the like, it is preferable that a distal end region of a bending portion is curved first to easily determine an insertion direction of an insertion portion in order to easily insert the insertion portion into a deep part of the bronchi.

Therefore, for example, International Publication No. 2013-190910 discloses an endoscope in which a bending tube formed by a hyperelastic tube body is provided in a bending portion to allow the bending portion to curve first.

International Publication No. 2013-190910 discloses a technique of the endoscope including: a plurality of slits formed on the bending tube; and a wire guide provided on an inner circumference of the bending tube, wherein slit intervals in a center region are formed longer than slit intervals of a distal end side region to allow the bending portion to curve first.

SUMMARY OF THE INVENTION

An aspect of the present invention provides a bending portion for endoscope including: a distal end side bending tube to which a plurality of bending pieces are continuously and pivotably coupled; a proximal end side bending tube coupled to a proximal end side of the distal end side bending tube and including a bending element with a bending moment for obtaining a predetermined bending angle greater than a bending moment of the distal end side bending tube; an outer coat covering the distal end side bending tube and the proximal end side bending tube; an operation wire including a distal end which is fixed to a wire fixing portion located on one of the bending pieces on a distalmost end of the distal end side bending tube, the operation wire actively bending the distal end side bending tube and the proximal end side bending tube by pulling and relaxing; and a wire receiving portion into which the operation wire is inserted.

An aspect of the present invention provides an endoscope including: a distal end side bending tube in which a plurality of bending pieces are continuously and pivotably coupled; a proximal end side bending tube coupled to a proximal end side of the distal end side bending tube and including a bending element with a bending moment for obtaining a predetermined bending angle greater than a bending moment of the distal end side bending tube; an outer coat covering the distal end side bending tube and the proximal end side bending tube; an operation wire including a distal end which is fixed to a wire fixing portion located on one of the bending pieces on a distalmost end of the distal end side bending tube, the operation wire actively bending the distal end side bending tube and the proximal end side bending tube by pulling and relaxing; and a wire receiving portion into which the operation wire is inserted, wherein the endoscope further includes an insertion portion including a bending portion for endoscope in which the distal end side bending tube and the proximal end side bending tube actively bend by pulling and relaxing of the operation wire.

DETAILED DESCRIPTION OF THE PREFERRED EMBODIMENT(S)

(Configuration)

Figure 1:
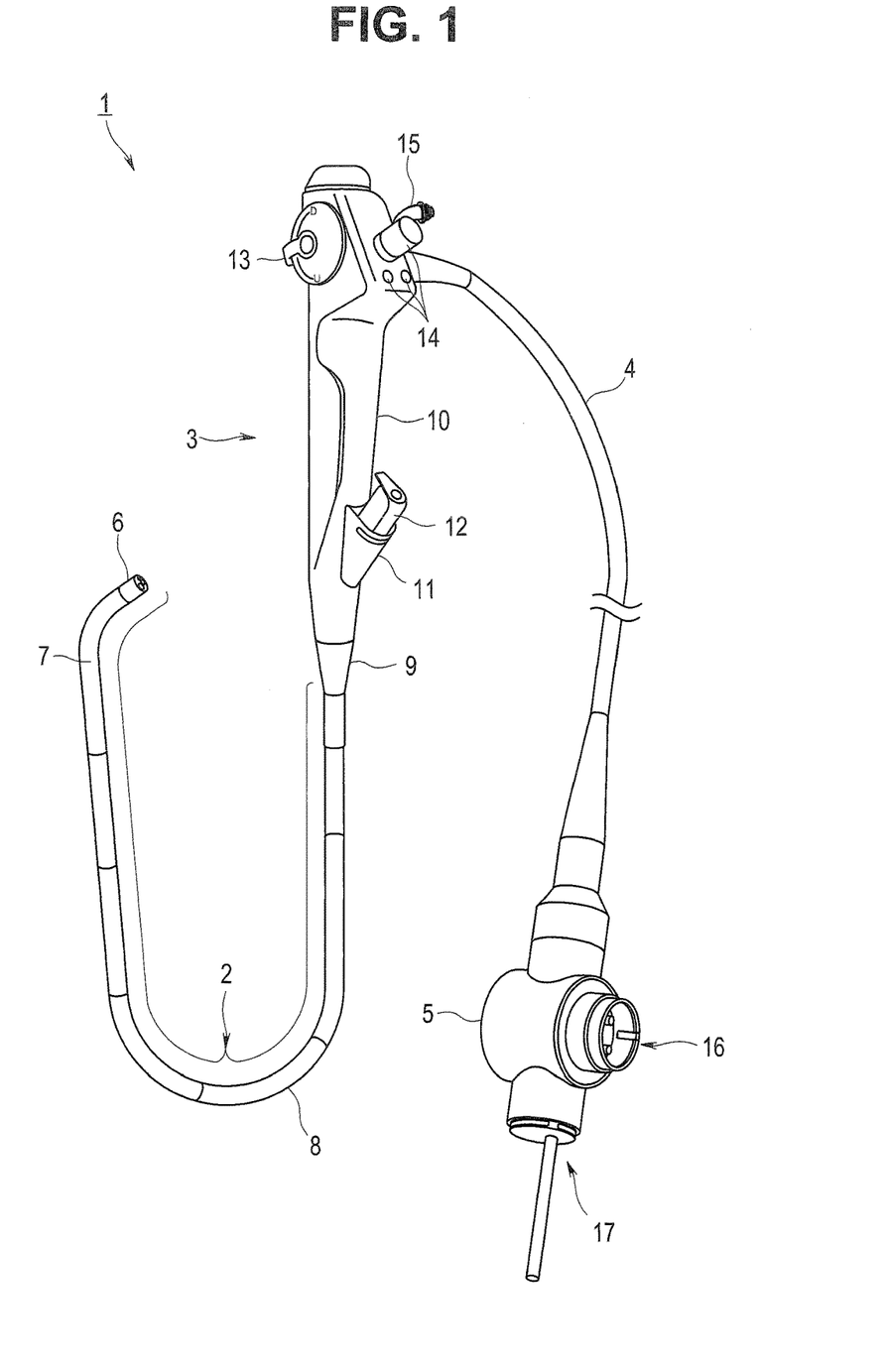
FIG. 1 is a general view of an endoscope.

Hereinafter, an embodiment of the present invention will be described with reference to the drawings. The drawings relate to an embodiment of the present invention. As shown in FIG. 1, an electronic endoscope (hereinafter, simply called an endoscope) 1 of the present embodiment mainly includes: an insertion portion 2 formed in an elongated tubular shape; an operation portion 3 consecutively connected to a proximal end of the insertion portion 2; a universal cord 4 that is an endoscope cable extended from the operation portion 3; an endoscope connector 5 located on a distal end of the universal cord 4; and the like.

In order from a distal end side, a distal end portion 6, a bending portion 7, and a flexible tube portion 8 are consecutively connected to and formed on the insertion portion 2, and the insertion portion 2 is a flexible tubular member. In the distal end portion 6 among the components, an image pickup unit that is an image pickup apparatus not shown including image pickup means inside, illumination means, and the like are housed and arranged.

The bending portion 7 includes a first bending portion 7a on the distal end side and a second bending portion 7b consecutively connected to a proximal end of the first bending portion 7a. The bending portion 7 is a mechanical section that can be actively bent in two up and down directions (UP-DOWN) by turning operation of a bending lever 13 described later among operation members of the operation portion 3.

Note that the bending portion 7 is not limited to this type, and the bending portion 7 may be a type that can be bent in four directions including left and right directions in addition to the up and down directions (entire circumferential directions around the axis based on up, down, left, and right operations, UP-DOWN/RIGHT-LEFT).

The flexible tube portion 8 is a tubular member formed with softness to allow the flexible tube portion 8 to be passively flexible. Other than a treatment instrument insertion channel, various signal lines extended from the image pickup apparatus built in the distal end portion 6 and further extended into the universal cord 4 from the operation portion 3, a light guide for guiding illumination light from a light source apparatus to emit the illumination light from the distal end portion 6, and the like are inserted into the flexible tube portion 8 (these are not shown).

The operation portion 3 includes: a bend preventing portion 9 provided on the distal end side, covering a proximal end of the flexible tube portion 8, and connected to the flexible tube portion 8; a grasping portion 10 consecutively connected to the bend preventing portion 9 and grasped by a hand of a user in using the endoscope 1; operation means for operating various endoscopic functions provided on an outer surface of the grasping portion 10; a treatment instrument insertion portion 11; and a suction valve 15.

Examples of the operation means provided on the operation portion 3 include: the bending lever 13 for performing bending operation of the bending portion 7; and a plurality of operation members 14 for performing air/water feeding operation, suction operation, or each operation corresponding to the image pickup means, the illumination means, and the like.

The treatment instrument insertion portion 11 includes a treatment instrument insertion port for inserting various treatment instruments not shown and is a configuration portion communicating with a treatment instrument insertion channel through a branch member inside of the operation portion 3. A forceps plug 12 that is a lid member for opening and closing the treatment instrument insertion port and that is detachable (replaceable) from the treatment instrument insertion portion 11 is located on the treatment instrument insertion portion 11.

The universal cord 4 is a composite cable in which various signal lines and the like inserted from the distal end portion 6 of the insertion portion 2 to the operation portion 3 through the inside of the insertion portion 2 and further extended from the operation portion 3 are inserted inside, a light guide bundled connected to a light source apparatus not shown is inserted, and a tube for air/water feeding not shown extended from an air/water feeding apparatus is further inserted.

The endoscope connector 5 includes: an electrical connector portion 16 on a side surface portion, the electrical connector portion 16 connected with a signal cable for connecting a video processor of an external device not shown; a light source connector portion 17 connected with a light guide bundle and an electrical cable not shown for connecting a light source apparatus that is an external device; an air/water feeding plug (not shown) for connecting a tube for air/water feeding (not shown) from an air/water feeding apparatus that is an external device not shown; and the like.

Here, a configuration of the bending portion 7 provided on the insertion portion 2 of the endoscope 1 of the present embodiment will be described with reference to FIGS. 2 to 5. Note that in the following description, a well-known configuration of the insertion portion 2, the distal end portion 6, and the flexible tube portion 8 will not be described.

Figure 2:
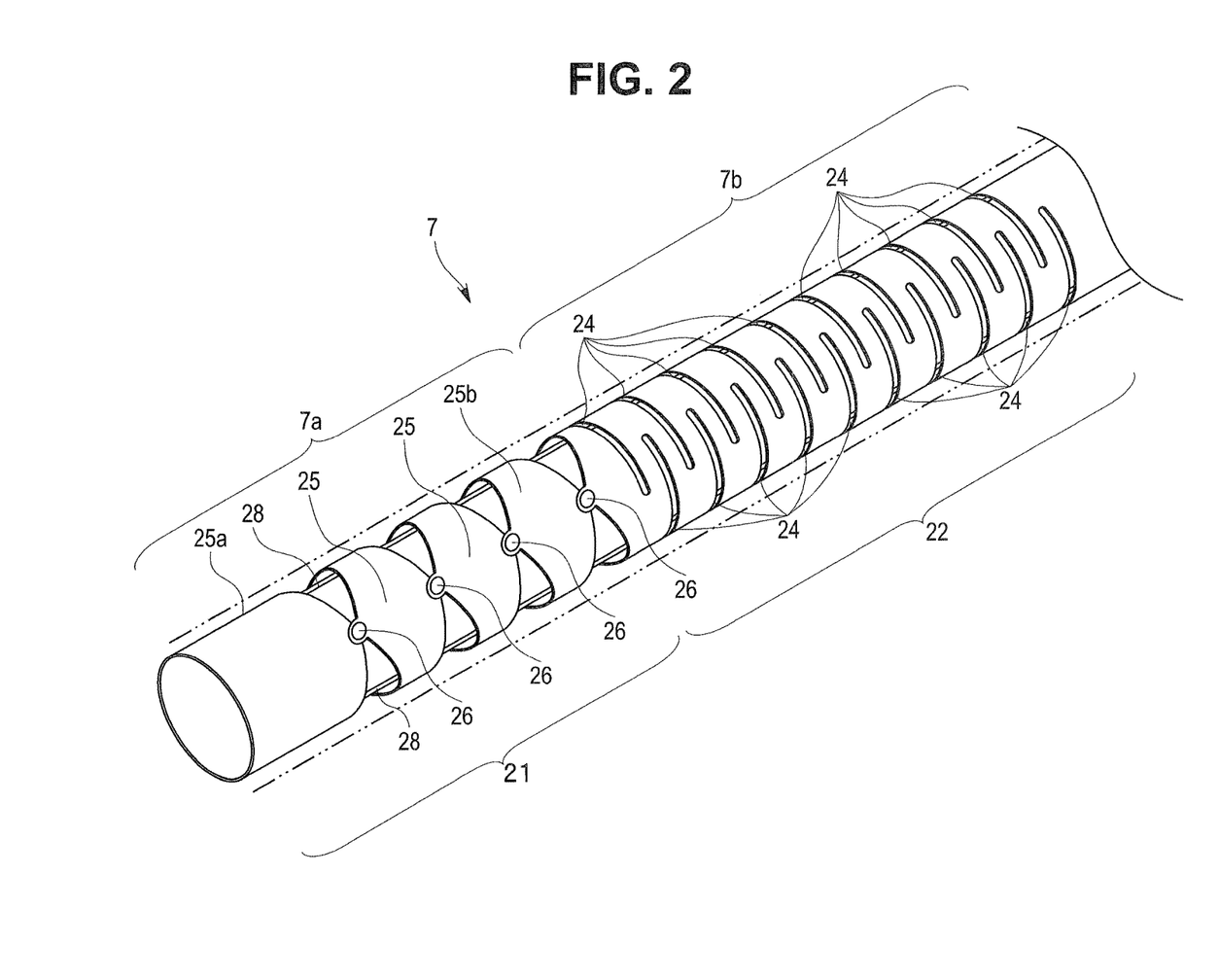
FIG. 2 is a perspective view mainly showing a first bending portion and a second bending portion.
Figure 3:
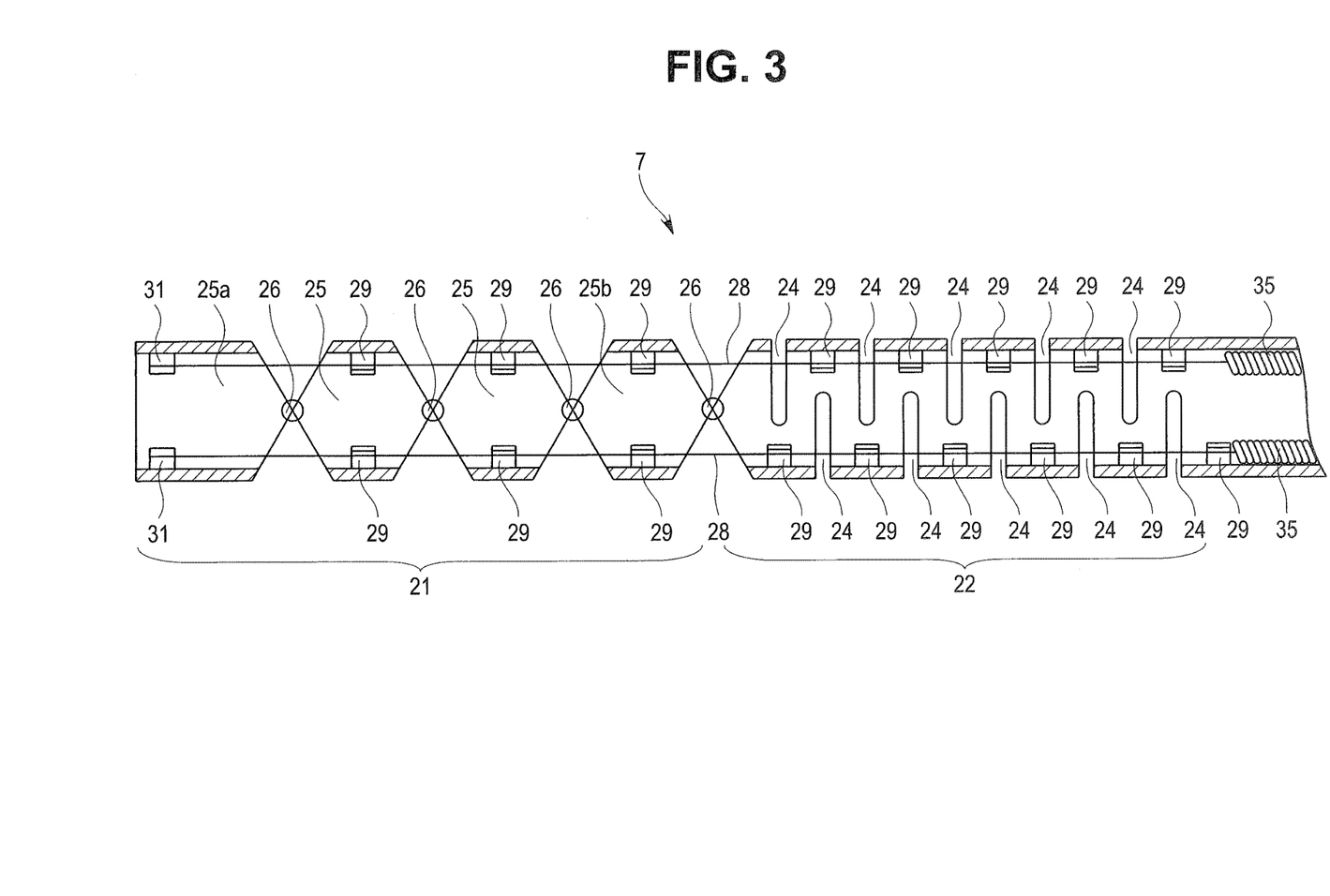
FIG. 3 is a cross-sectional view mainly showing the first bending portion and the second bending portion.

FIG. 2 is a perspective view mainly showing the first bending portion and the second bending portion, and FIG. 3 is a cross-sectional view mainly showing the first bending portion and the second bending portion. As shown in FIGS. 2 and 3, in the bending portion 7, a first bending tube 21 that is a distal end side bending tube is located in the first bending portion 7a on the distal end side, and a second bending tube 22 that is a proximal end side bending tube is located in the second bending portion 7b on the proximal end side.

Note that the bending portion 7 is covered by a steel tube that is a bending braid not shown, an outer coat that is bending rubber, and the like so as to cover around the first bending tube 21 and the second bending tube 22.

In the first bending tube 21, a plurality of bending pieces 25 are pivotably coupled through pivotal portions 26 such as rivets, and the first bending tube 21 has a predetermined length in an insertion axis direction of the insertion portion 2.

The bending pieces 25 are funned in a substantially circular tube shape, and respective both end center parts are pivotably coupled through the pivotal portions 26. A bending piece 25a at a distalmost end is coupled to the distal end portion 6 of the insertion portion 2, and a bending piece 25b at a proximalmost end is pivotably coupled through the pivotal portion 26 on the distal end of the second bending tube 22.

Note that in the plurality of bending pieces 25, a plurality of, two here, wire guides 29 that are wire receiving portions are located in an inner circumference portion of each bending piece 25 (see FIG. 3). The two wire guides 29 are provided at up and down positions rotated substantially 90 degrees about a center axis of the bending piece 25, from the section coupled by the pivotal portion 26 in one bending piece 25.

Operation wires 28 pulled and relaxed to move back and forth by operation of the bending lever 13 provided on the operation portion 3 are inserted into the respective wire guides 29 provided on the plurality of bending pieces 25. Note that two wire fixing portions 31 on which respective distal ends of a plurality of, two here, operation wires 28 are fixed are located on the bending piece 25a at the distalmost end.

The operation wires 28 are inserted into coil tubes 35 in the flexible tube portion 8 consecutively connected to the proximal end of the bending portion 7 and in the operation portion 3. Distal ends of the coil tubes 35 are arranged to position at a boundary part of the bending portion 7 and the flexible tube portion 8, and the coil tubes 35 are protection members configured to protect the operation wires 28 and various constituent elements in the insertion portion 2 and the operation portion 3.

The second bending tube 22 is arranged on the proximal end side of the first bending tube 21 and is a member mainly including a cylindrical bending tube main body as a bending element formed by a hyperelastic alloy.

Here, examples of a hyperelastic alloy material included in the second bending tube 22 include Ni—Ti (nickel titanium), a titanium alloy, beta titanium, pure titanium, 64 titanium, and A7075.

The second bending tube 22 is provided with a plurality of bending slits 24 with a basic shape of a partially circular long hole extending in a circumferential direction of the second bending tube 22, and the bending slits 24 are provided by, for example, laser processing, at predetermined intervals in the insertion axis direction of the insertion portion 2.

The plurality of bending slits 24 are alternately formed on up and down positions in a direction orthogonal to a longitudinal direction of the bending tube 22.

A plurality of wire guides 29 are also located in an inner circumference portion of the second bending tube 22, just like the bending pieces 25. The plurality of wire guides 29 are provided between the plurality of bending slits 24 on up and down positions of the second bending tube 22.

In the plurality of wire guides 29, a plurality of, two here, operation wires 28 are also inserted on up and down positions in the second bending tube 22.

(Action)

As illustrated in the configuration, in the bending portion 7, the first bending tube 21 of the piece type is arranged on the first bending portion 7a on the distal end side, the first bending tube 21 including the plurality of bending pieces 25 pivotably coupled through the pivotal portions 26. The second bending tube 22 of the slit type is arranged on the proximal end side of the first bending tube 21 of the piece type in the second bending portion 7b, the second bending tube 22 including the plurality of bending slits 24 formed in the hyperelastic tubes that are tubular members. Action including movement of the sections will be described below with reference to FIGS. 4 to 7.

Figure 4:
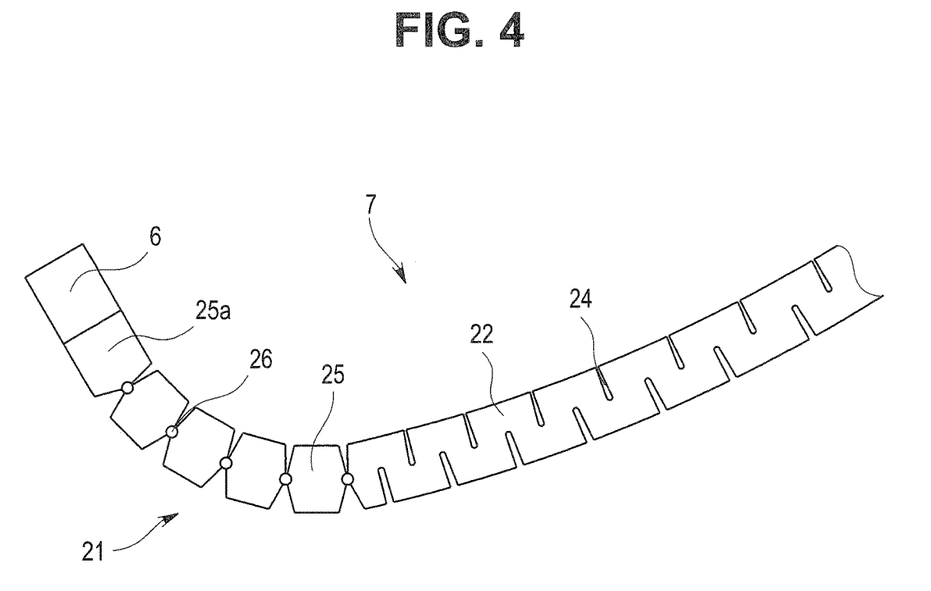
FIG. 4 is a diagram showing a state that a bending portion is bent toward an UP-side.
Figure 5:
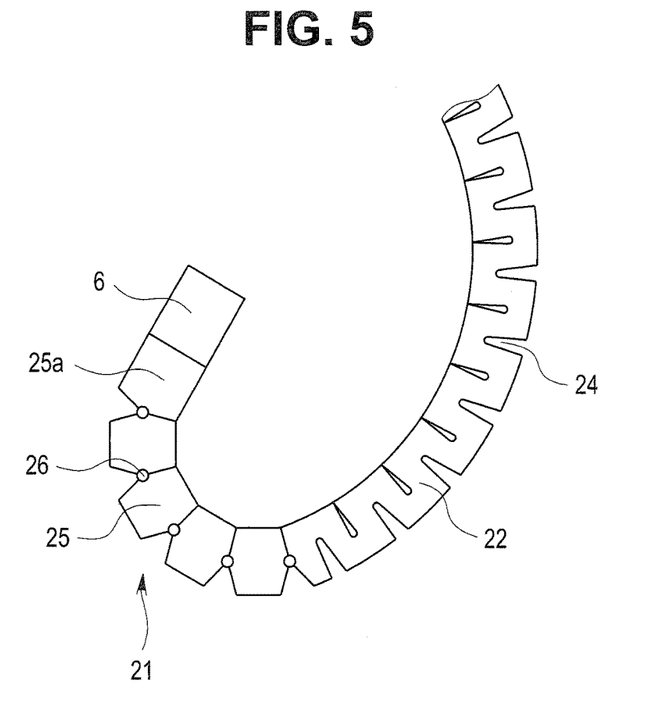
FIG. 5 is a diagram showing a state that the bending portion is further bent in an UP-direction from a state that the bending portion of FIG. 4 is bent.
Figure 6:
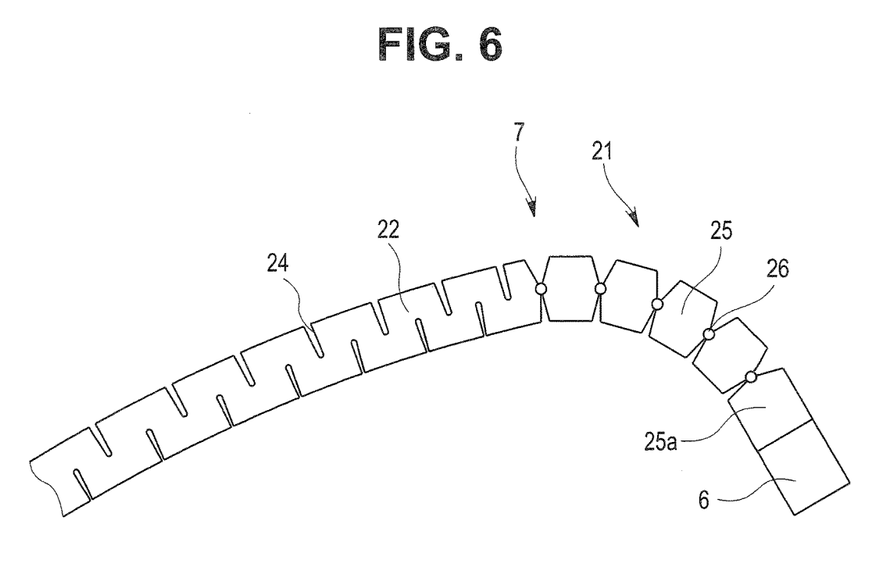
FIG. 6 is a diagram showing a state that the bending portion is bent toward a DOWN-side.
Figure 7:
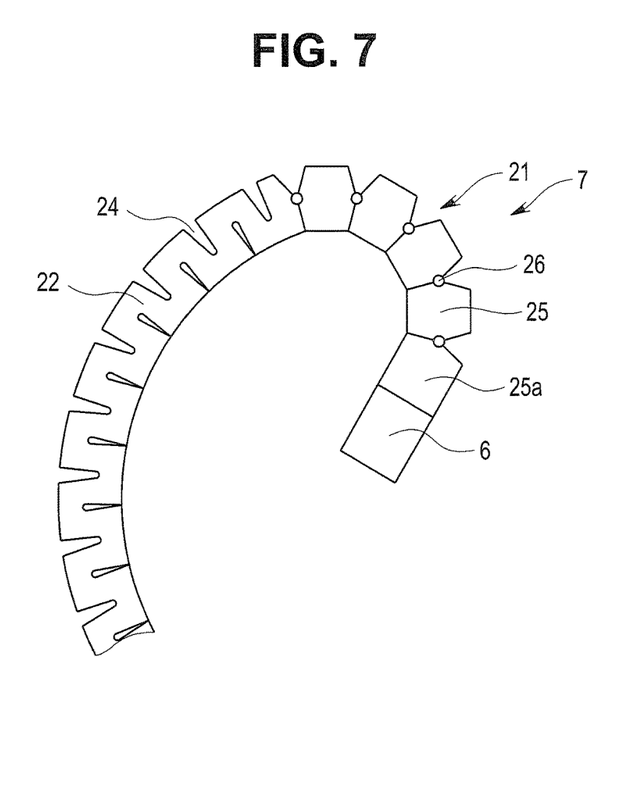
FIG. 7 is a diagram showing a state that the bending portion of FIG. 6 is further bent in a DOWN-direction.

FIG. 4 shows a state that the bending portion is bent toward an UP-side. FIG. 5 shows a state that the bending portion is further bent in the UP-direction from a state that the bending portion of FIG. 4 is bent. FIG. 6 shows a state that the bending portion is bent toward a DOWN-side. FIG. 7 shows a state that the bending portion of FIG. 6 is further bent in the DOWN-direction.

In the bending portion 7, when the plurality of, two here, operation wires 28 move back and forth through turn operation of the bending lever 13 of the operation portion 3 in a predetermined direction, the bending portion 7 actively bends as shown in FIGS. 4 to 7, because the distal end side of each operation wire 28 is fixed on the distal end side of the distalmost end piece 25a.

In the bending action, the first bending portion 7a on the distal end side of the bending portion 7 curves faster and curves more easily than the second bending portion 7b on the proximal end side provided with the second bending tube 22 inside, due to the first bending tube 21 of the piece type provided inside.

That is, unlike the first bending portion 7a on the distal end side of the bending portion 7, the second bending tube 22 of the slit type provided inside is formed by a hyperelastic body in the second bending portion 7b on the proximal end side of the bending portion 7. Therefore, a bending moment of the second bending portion 7b on the proximal end side is stronger than that of the first bending portion 7a on the distal end side, and it is hard to curve the second bending portion 7b on the proximal end side.

Therefore, the bending portion 7 is formed such that a speed of curving of the second bending portion 7b on the proximal end side is slower than that on the distal end side.

As a result, in a first motion in which the bending lever 13 of the operation portion 3 is operated, the first bending portion 7a located on the distal end side curves first with a small radius of curvature in the bending portion 7 as shown in FIG. 4 or 6. Next, the second bending portion 7b located on the proximal end side is acts to curve with a larger radius of curvature than the first bending portion 7a on the distal end side.

Here, a difference between maximum bending angles of the first bending portion 7a and the second bending portion 7b of the bending portion 7 will be described in detail. In the bending portion 7 here, the maximum bending angle of the first bending portion 7a on the distal end side is about 120 degrees based on setting of a turn range of the plurality of bending pieces 25 included in the first bending tube 21.

In the bending portion 7, the maximum bending angle of the second bending portion 7b on the proximal end side is about 90 degrees based on setting of formation intervals of the plurality of bending slits 24 that are hyperelastic tubes included in the second bending tube 22.

Note that when the first bending tube 21 makes a bending action first due to the turn of the plurality of bending pieces 25 (FIG. 4 or 6) in the first motion in the bending operation of the bending portion 7, and the bending operation is further performed, the first bending portion 7a on the distal end side bends at the maximum bending angle of about 120 degrees, earlier than the second bending portion 7b.

In the bending portion 7, the second bending portion 7b provided with the second bending tube 22 including the plurality of bending slits 24 formed on the hyperelastic tube is bent at the maximum bending angle of about 90 degrees (FIG. 5 or 7), and the first bending portion 7a and the second bending portion 7b are bent to the maximum extent as a whole which is about 210 degrees in total.

In this way, the reason that the maximum bending angle of the first bending portion 7a on the distal end side of the bending portion 7 is about 120 degrees is that a maximum angle of branch angles of complicated bronchi is about 120 degrees when the endoscope 1 is a bronchoscope, and a directionality of the insertion direction of the distal end portion 6 of the insertion portion 2 at the bending operation can be easily determined. This improves the bending operability and improves the insertion property of the insertion portion 2 into the bronchi.

(Advantageous Effects)

According to the description, when the endoscope 1 of the present embodiment is bent and operated by the bending lever 13 of the operation portion 3, the first bending portion 7a on the distal end side of the bending portion 7 provided on the insertion portion 2 starts to bend earlier than the second bending portion 7b on the proximal end side.

That is, the endoscope 1 is formed such that the first bending portion 7a on the distal end side starts to bend first before the second bending portion 7b on the proximal end side of the bending portion 7 when the insertion portion 2 is inserted into a complicated body cavity, such as bronchus, and small turns of the insertion portion 2 are possible.

As a result, the endoscope 1 can easily adjust the form of the bending portion 7 to the shape of a complicated body cavity wall, such as bronchus, by little operation of the bending lever 13 provided on the operation portion 3, and bending adjustment of the bending portion 7 in the bending operation becomes easy. Therefore, the operability in the bending operation of the bending portion 7 is further improved in the endoscope 1.

Furthermore, when the bending lever 13 of the operation portion 3 is further operated in the endoscope 1, the first bending portion 7a bends at about 120 degrees that is the maximum bending angle, and then the second bending portion 7b bends at about 90 degrees that is the maximum bending angle.

The bending portion 7 is bent to the maximum extent which is about 210 degrees that is the sum of the respective maximum bending angles of the first bending portion 7a and the second bending portion 7b.

That is, the endoscope 1 is formed such that when the distal end side and the proximal end side of the bending portion 7 are bent to the maximum extent, a radius of curvature of the first bending portion 7a on the distal end side is small, and a radius of curvature of the second bending portion 7b on the proximal end side is large.

As a result, the insertion property of the insertion portion 2 into a complicated body cavity, such as bronchus, is improved in the endoscope 1, and the endoscope 1 can prevent the second bending portion 7b on the proximal end side of the bending portion 7 of the insertion portion 2 from coming into contact with and applying force to the body cavity wall. Therefore, unnatural feeling, pain, and the like of the patient can be reduced.

(Modifications)

Figure 8:
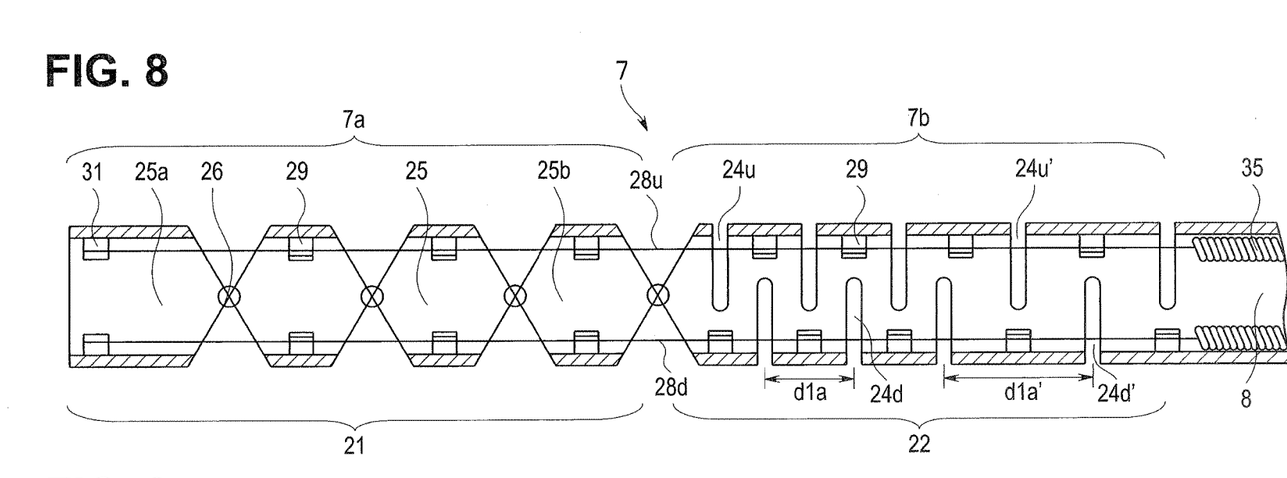
FIG. 8 is a cross-sectional view showing a structure of bending slits provided on a hyperelastic tube of the second bending portion and an arrangement and a shape of the slits according to a first modification.
Figure 9:
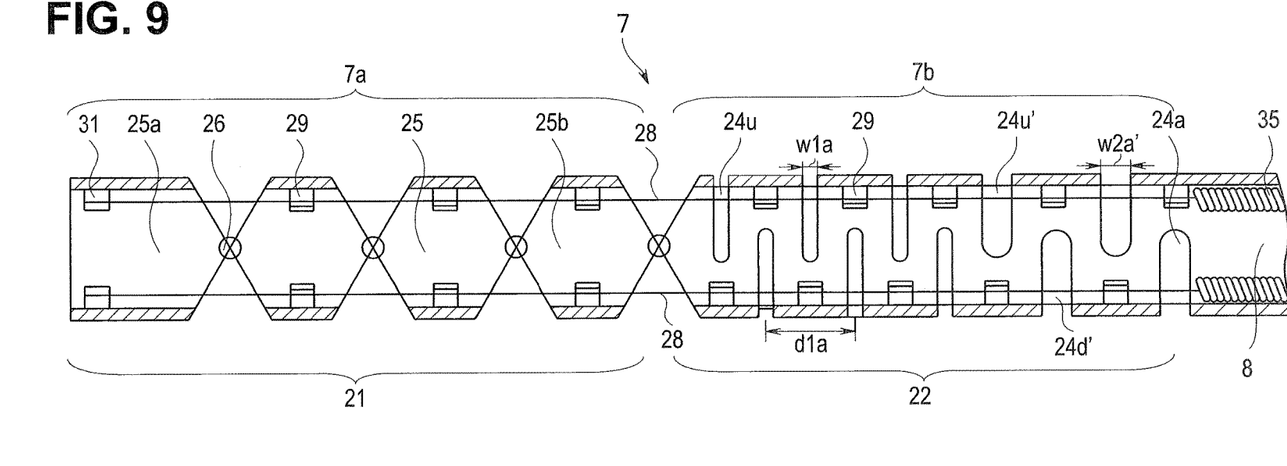
FIG. 9 is a cross-sectional view showing a structure of bending slits provided on the hyperelastic tube of the second bending portion and an arrangement and a shape of the slits according to a second modification.
Figure 10:
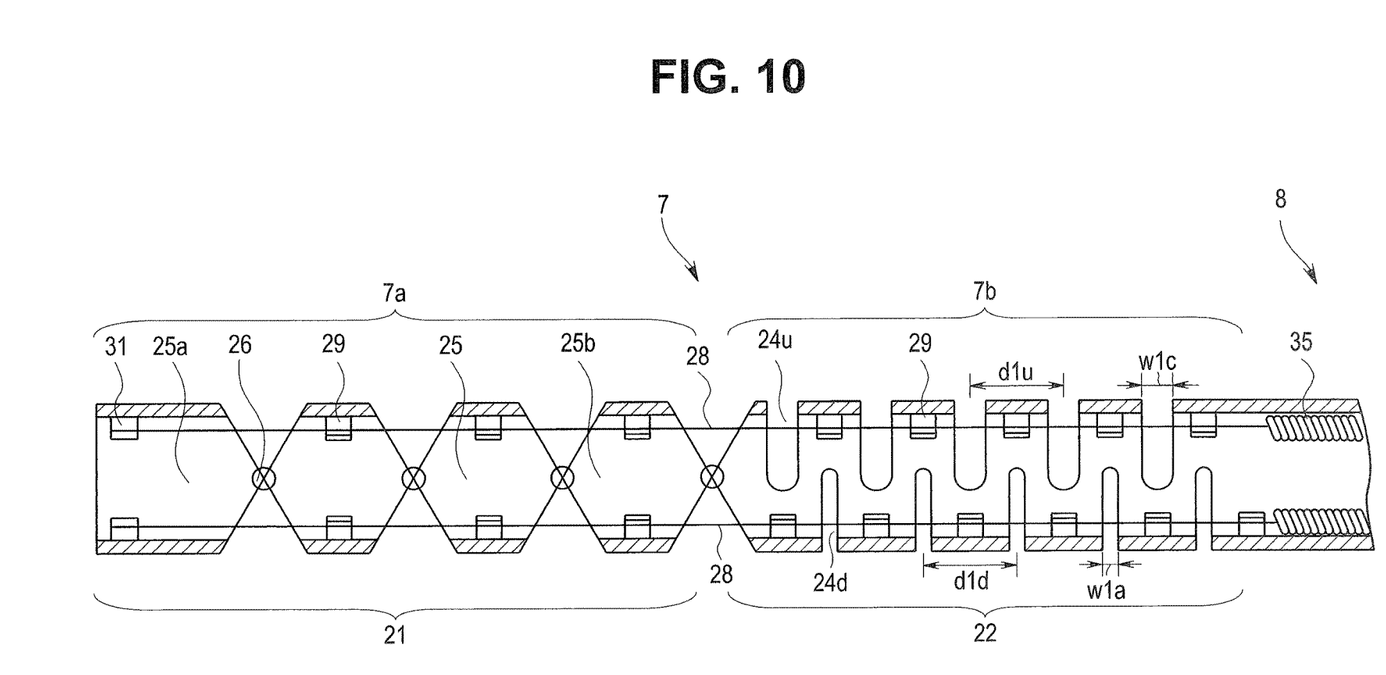
FIG. 10 is a cross-sectional view showing a structure of bending slits provided on the hyperelastic tube of the second bending portion and an arrangement and a shape of the slits according to a third modification.

FIGS. 8, 9, and 10 illustrate structures of the bending slits 24 provided on the hyperelastic tube of the second bending portion 7b. FIGS. 8, 9, and 10 show differences in the arrangement or the pattern of the shape of the respective (first) bending slits 24.

For the regularity of patterns, intervals (pitches) between adjacent notches in a plurality of notches provided in the longitudinal direction of the hyperelastic tube and notch widths of the plurality of respective notches change in the longitudinal direction of the hyperelastic tube (insertion portion 2) as can be understood from modifications described below.

Figure 11:
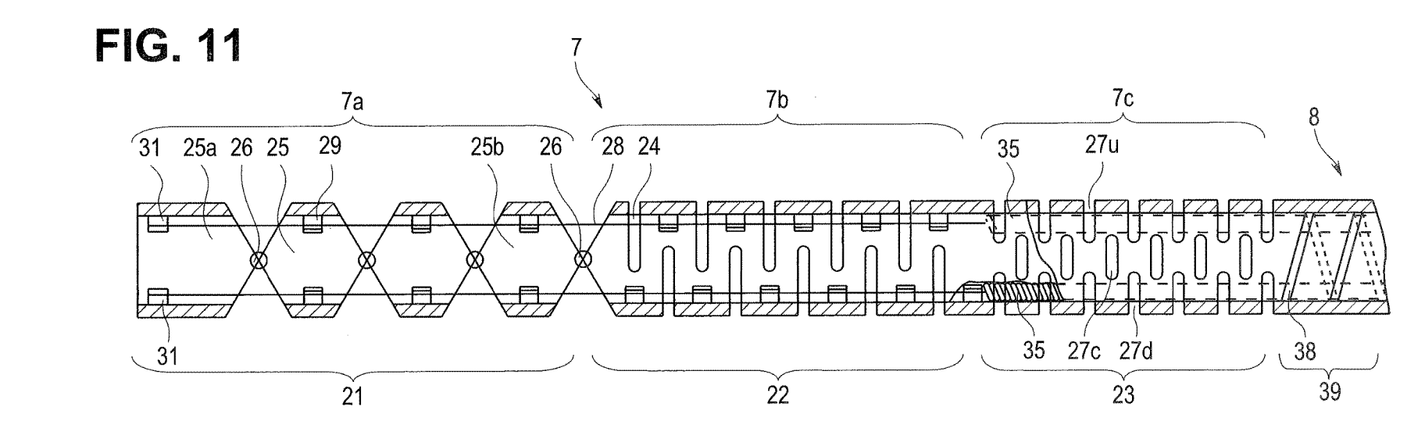
FIG. 11 is a diagram showing an arrangement and a shape of bending slits included in the first bending portion, the second bending portion, and a third bending portion and showing a flexible tube according to a fourth modification.
Figure 12:
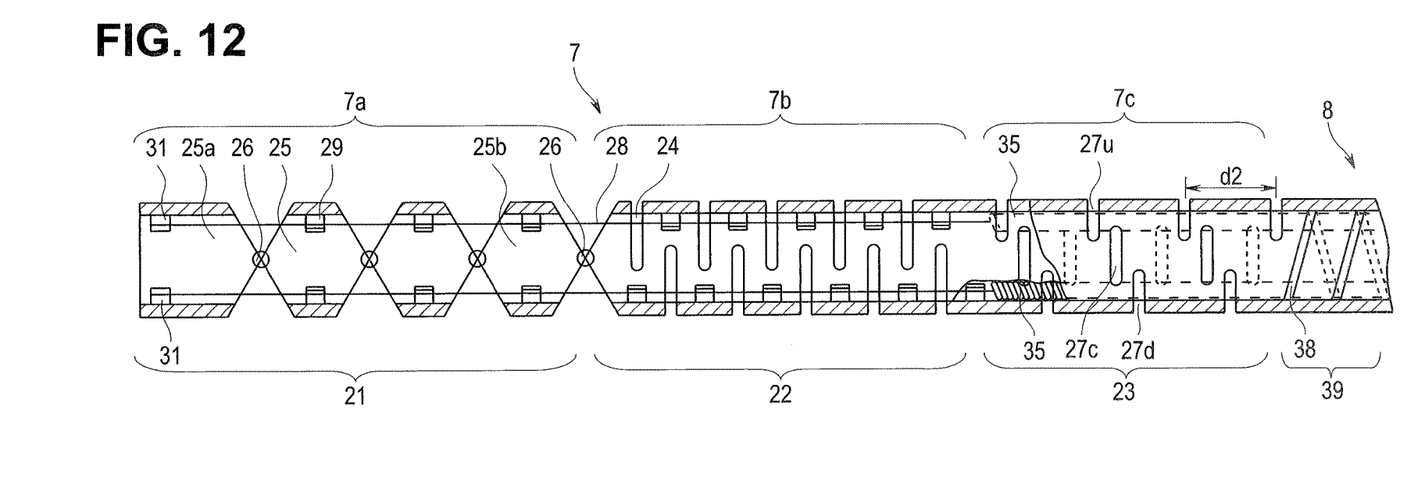
FIG. 12 is a diagram showing an arrangement and a shape of bending slits included in the first bending portion, the second bending portion, and the third bending portion and showing the flexible tube according to a fifth modification.

Note that FIGS. 11 and 12 illustrate structures in which a passive bending portion is provided on a proximal end of the second bending portion 7b of the bending portion 7 of the insertion portion 2.

(First Modification)

First, a first modification of the modifications will be described.

In FIG. 8 as the first modification, the pattern of the bending slits provided on the hyperelastic tube forming the second bending tube 22 is not constant in the longitudinal direction of the hyperelastic tube, and the structure changes in the middle.

In an example illustrated in FIG. 8, first bending slits 24u and 24d on a front side and second bending slits 24u' and 24d' on a back side are formed on the second bending tube 22 provided on the second bending portion 7b.

The first bending slits 24u and 24d on the front side are formed, for example, in the same way as the bending slits 24 in the second bending tube 22 shown in FIG. 3, and the second bending slits 24u' and 24d' on the back side are provided for proper lengths on parts on a backward side of the positions of the first bending slits 24u and 24d provided for predetermined lengths.

The second bending slits 24u' and 24d' on the back side are formed such that an interval d1a' in the longitudinal direction of the second bending tube 22 is greater than an interval d1a of the first bending slits 24u and 24d on the front side.

According to the configuration, the second bending portion 7b has a structure as shown in FIG. 8, and when the operation wire 28u or 28d is pulled, the part of the front side in the second bending tube 22 provided with the first bending slits 24u and 24d can be more largely bent. On the other hand, the amount of bending of the part of the back side in the second bending tube 22 provided with the second bending slits 24u' and 24d' is suppressed in the second bending portion 7b. According to the configuration, the endoscope 1 has an advantageous effect that the insertion portion 2 can be easily inserted into a largely curved body cavity.

(Second Modification)

Although the intervals d1a' of the second bending slits 24u' and 24d' provided in the longitudinal direction of the second bending tube 22 are changed to be different from the intervals d1a of the first bending slits 24u and 24d in FIG. 8, the width (that is, notch width) of the second bending slits 24u' and 24d' on the back side may be changed as in a second modification shown in FIG. 9.

In an example illustrated in FIG. 9, a notch width w2a' of the second bending slits 24u' and 24d' on the back side is greater than a notch width w1a of the first bending slits 24u and 24d on the front side. Note that the intervals of providing the second bending slits 24u' and 24d' on the back side in the longitudinal direction of the hyperelastic tube may also be changed or may not be changed.

The endoscope 1 of the present embodiment has the same or similar advantageous effects as in the case of the first modification shown in FIG. 8 depending on the size of the intervals and the width of the notches of the first bending slits 24u and 24d and the second bending slits 24u' and 24d'.

(Third Modification)

Next, a third modification of the modifications will be described.

In the first modification and the second modification, only the positions in the longitudinal direction are displaced in the first bending slits 24u and the second bending slits 24d formed on the second bending tube 22 provided in the second bending portion 7b, and the notches are substantially the same. In the present modification, for example, a notch width w1c of the first bending slits 24u in the upper direction is greater than the notch width w1a of the second bending slits 24d in the lower direction, as shown in FIG. 10.

Note that intervals (pitches) d1u and d1d of the first bending slits 24u and the second bending slits 24d in the longitudinal direction of the second bending tube 22 have the same values.

According to the structure, when the operation wire 28u or 28d is pulled, the amount of bending in the upper direction can be greater than the amount of bending in the lower direction.

This allows selective use of bending, such as using the bending in the upper direction when large bending is necessary and using the bending in the lower direction when large bending is not necessary.

Note that the flexible tube portion 8 is the same as in the embodiment described above.

(Fourth Modification)

Next, a fourth modification of the modifications will be described.

As shown in FIG. 11, the bending portion 7 of the insertion portion 2 of the endoscope 1 of the present modification is provided with the first bending portion 7a and the second bending portion 7b that are active bending portions and a third bending portion 7c that is a passive bending portion.

More specifically, the first bending tube 21 and the second bending tube 22 formed by a hyperelastic tube are provided in the first bending portion 7a and in the second bending portion 7b that are active bending portions as described above, and a third bending tube 23 formed by a hyperelastic tube is further provided in the third bending portion 7c. That is, the insertion portion 2 here includes the third bending portion 7c that is a passive bending portion not included in the embodiments so far, throughout a predetermined length in the longitudinal direction from a back end of the second bending portion 7b provided with the second bending tube 22, and the flexible tube portion 8 is further provided on the proximal end side of the third bending portion 7c.

The second bending portion 7b, the third bending portion 7c, and the flexible tube portion 8 are provided with the second bending tube 22, the third bending tube 23, and a spiral tube 39 integrally formed by a hyperelastic tube inside.

The third bending tube 23 provided on the third bending portion 7c that is a passive bending portion includes passive bending slits 27u and 27d symmetrically formed in the up and down directions along the longitudinal direction.

The passive bending slits 27u and 27d are formed in a length slightly shorter than a half of a length of a circular tube surface of the third bending tube 23 in the circumferential direction.

The third bending tube 23 also includes passive bending slits 27c provided symmetrically in the left and right directions in the circumferential direction, the passive bending slits 27c bendable in the left and right directions.

In this way, the passive bending slits 27u, 27d, and 27c formed on the third bending tube 23 allow the third bending portion 7c to easily curve (bend) in the up, down, left, and right directions.

The spiral tube 39 provided with spiral slits 38 in a hyperelastic tube is located on the flexible tube portion 8 consecutively connected to the back side of the passive bending portion 7c.

(Fifth Modification)

FIG. 12 shows a modification of the structure of the passive bending slits formed on the third bending tube 23 provided on the third bending portion 7c that is a passive bending portion. That is, the structure of the passive bending slits 27u, 27d, and 27c provided on the third bending tube 23 of the third bending portion 7c forming the passive bending portion described in the fourth modification is changed in the present modification.

The passive bending slits in the present modification include the passive bending slits 27u, 27d, and 27c formed along a spiral in the longitudinal direction on a cylindrical surface of the third bending tube 23. That is, in the present modification, the passive bending slits 27u, 27d, and 27c are periodically formed, discretely along the spiral.

The pitch of the spiral is d2 in an example illustrated in FIG. 12. In the example illustrated in FIG. 12, the passive bending slits 27u, 27d, and 27c are periodically formed in the bending direction (up and down directions) in which the second bending portion 7b is bendable, and the second bending portion 7b can be easily bent (curved) in the direction. The passive bending slits 27u, 27d, and 27c are periodically formed such that the second bending portion 7b can also be easily bent (curved) in other directions.

Here, the spiral tube 39 provided with the spiral slits 38 on a hyperelastic tube is also located on the flexible tube portion 8 consecutively connected to the back side of the passive bending portion 7c.

Note that although FIG. 12 shows a configuration in which the passive bending portion 7c in FIG. 11 is modified, the configurations may also be applied to one of the modifications in FIGS. 8, 9, and 10.

Furthermore, although the bending directions of the first bending portion 7a and the second bending portion 7b as active bending portions in the bending portion 7 are the up and down (UP, DOWN) directions in the present embodiment, the bending directions are not limited to these, and the first bending portion 7a and the second bending portion 7b may be bent in four directions including the left and right (LEFT-RIGHT) directions.

Note that the invention described in the embodiment is not limited to the embodiment, and various modifications can also be carried out in an execution phase without departing from the scope of the invention.

What is claimed is:

1. A bending portion for an endoscope comprising:
   a distal end side bending tube in which a plurality of separate bending pieces are pivotably coupled through pivot joints connecting adjacent ones of the plurality of bending pieces, the distal end side bending tube being configured to have a first bending moment for obtaining a predetermined bending angle in each of at least two directions, the at least two directions being from a central axis of the distal end side bending tube when the distal end side bending tube is in an unbent configuration;
   a proximal end side bending tube coupled to a proximal end side of the distal end side bending tube and comprising a bending element the bending element being configured to have a second bending moment for obtaining the predetermined bending angle, the second bending moment being greater than the first bending moment of the distal end side bending tube;
   an outer coat covering the distal end side bending tube and the proximal end side bending tube;
   a plurality of operation wires, each including a distal end which is fixed to a wire fixing portion located on one of the bending pieces on a distalmost end of the distal end side bending tube, the operation wires actively bending the distal end side bending tube and the proximal end side bending tube in the at least two directions by pulling and relaxing; and a plurality of wire receiving portions into which the plurality of operation wires are respectively inserted wherein the bending element includes a tubular member, and the tubular member includes a plurality of slits formed in a circumferential direction of the tubular member.

2. The bending portion according to claim 1, wherein the tubular member is a hyperelastic tube.

3. The bending portion according to claim 2, wherein the hyperelastic tube is made of NiTi.

4. The bending portion according to claim 3, further comprising a passive bending tube consecutively connected to a proximal end of the proximal end side bending tube.

5. The bending portion according to claim 4, wherein the proximal end side bending tube and the passive bending tube are integrally formed by the tubular member.

6. The endoscope comprising an elongated body, the elongated body comprising the bending portion according to claim 1.

* * * * *

UNITED STATES PATENT AND TRADEMARK OFFICE
CERTIFICATE OF CORRECTION

PATENT NO. : 10,149,608 B2
APPLICATION NO. : 15/355138
DATED : December 11, 2018
INVENTOR(S) : Kiwamu Fujitani Page 1 of 1

It is certified that error appears in the above-identified patent and that said Letters Patent is hereby corrected as shown below:

In the Claims

Column 10, Claim 1, Line 57 should read:
comprising a bending element, the bending element Signed and Sealed this
Twenty-fifth Day of June, 2019

Andrei Iancu
*Director of the United States Patent and Trademark Office*